(12) United States Patent
Hermentin

(10) Patent No.: US 8,150,630 B2
(45) Date of Patent: Apr. 3, 2012

(54) METHOD FOR CHARACTERISATION OF THE QUALITY OF SIALOGLYCOPROTEINS VIA AN ISOFORM NUMBER I

(76) Inventor: Peter Hermentin, Marburg (DE)

(*) Notice: Subject to any disclaimer, the term of this patent is extended or adjusted under 35 U.S.C. 154(b) by 874 days.

(21) Appl. No.: 12/090,778

(22) PCT Filed: Oct. 18, 2006

(86) PCT No.: PCT/EP2006/010044
§ 371 (c)(1),
(2), (4) Date: Sep. 4, 2008

(87) PCT Pub. No.: WO2007/045453
PCT Pub. Date: Apr. 26, 2007

(65) Prior Publication Data
US 2009/0272655 A1    Nov. 5, 2009

(30) Foreign Application Priority Data
Oct. 21, 2005   (DE) .......................... 10 2005 050 580

(51) Int. Cl.
*G01N 33/48* (2006.01)
(52) U.S. Cl. ....................................................... 702/19
(58) Field of Classification Search .................. None
See application file for complete search history.

(56) References Cited

U.S. PATENT DOCUMENTS
6,096,555 A    8/2000    Hermentin et al.

FOREIGN PATENT DOCUMENTS
| | | |
|---|---|---|
| DE | 197 53 681 A1 | 7/1999 |
| EP | 0 596 321 A2 | 5/1994 |
| WO | WO 97/05490 A1 | 2/1997 |

OTHER PUBLICATIONS

Hermentin et al., "The Hypothetical N-Glycan Charge. A number to characterize protein n-glycosylation," Pharm. Pharmacol. Commun. 1999, 5: pp. 33-43.*
Behr-Gross et al., "Collaborative Study for the Establishment of Erythropoieting BRP Batch 2," *Pharmaeuropa Bio*, 23-33 (2004).
Goldman et al., "Monitoring Recombinant Human Interferon-Gamma N-Glycosylation During Perfused Fluidized-Bed and Stirred-Tank Batch Culture of CHO Cells," *Biotechnology and Bioengineering*, 60(5): 596-607 (1998).
Hermentin et al., "A Strategy for the Mapping of N-Glycans by High-Performance Capillary Electrophoresis," *Analytical Biochemistry*, 221: 29-41 (1994).
Hermentin et al., "The Hypothetical N-Glycan Charge: A Number that Characterizes Proteing Glycosylation," *Glycobiology*, 6(2): 217-230 (1996).
Hermentin et al., "The Hypothetical N-Glycan Charge. A Number to Characterize Protein N-Glycosylation," *Pharm. Pharmacol. Commun.*, 5: 33-43 (1999).
Kelly et al., "Development of Electrophoretic Conditions for the Characterization of Protein Glycoforms by Capillary Electrophoresis—Electrospray Mass Spectrometry," *J. of Chromatography A*, 720: 409-427 (1996).
Rose et al., "Definition and Measurement of Follicle Stimulating Hormone," *Endocrine Reviews*, 21(1):5-22 (2000).
Hermentin et al., "A Strategy for the Mapping of *N*-Glycans by High-pH Anion-Exchange Chromatography with Pulsed Amperometric Detection," *Analytical Biochemistry* 203, pp. 281-289 (1992).
Hermentin et al., "The Mapping by High-pH Anion-Exchange Chromatography with Pulsed Amperometric Detection and Capillary Electrophoresis of the Carbohydrate Moieties of Human Plasma $\alpha_1$-Acid Glycoprotein," *Analytical Biochemistry* 206, pp. 419-429 (1992).

* cited by examiner

*Primary Examiner* — Jason Sims
(74) *Attorney, Agent, or Firm* — Leydig, Voit & Mayer, Ltd.

(57) ABSTRACT

A method is described for characterization of the quality of a sialoglycoprotein via its isoform number I which is calculated from the isoform distribution of the capillary electrophoretic analysis of the sialoglycoprotein and represents a quality feature for the batch consistency, storage stability, biological half-life and the biological effectiveness of a therapeutic glycoprotein. Uses of this method are also described.

18 Claims, No Drawings

METHOD FOR CHARACTERISATION OF THE QUALITY OF SIALOGLYCOPROTEINS VIA AN ISOFORM NUMBER I

This patent application is a national phase of International Patent Application PCT/EP2006/010044, filed Oct. 18, 2006.

The subject of the present invention is a method for characterisation of the quality of sialoglycoproteins and also an in vitro method for determination of the bioavailability of sialoglycoproteins by means of capillary zone electrophoresis (CZE) which is based on the "isoform number", subsequently termed I, and can be used both for endogenous glycoproteins and exogenous glycoproteins.

Exogenous glycoproteins are in this context e.g. recombinant therapeutic glycoproteins, obtained from mammal cells, such as e.g. erythropoietin, follicle-stimulating hormone, chorionic gonadotrophin, tissue plasminogen activator or antithrombin III.

Endogenous glycoproteins in this context are human or non-human, e.g. bovine, serum glycoproteins, such as e.g. human $\alpha_1$-acidic glycoprotein, human transferring or bovine fetuin.

The research, development and production of therapeutic glycoproteins and also their official or clinical licensing demands complex analysis with respect to the in vivo half-life, biological safety, product definition and batch consistency.

In this respect, above all the proportion of sialic acid has played an important role to date as a parameter since it is known that the presence or absence of sialic acid crucially jointly determines the circulation half-life of a glycoprotein in the blood or its clearance.

In the case of erythropoietin (EPO), capillary zone electrophoresis (CZE) represents an important method for characterising the sialoglycoprotein and establishing its biological effectiveness. This examination is described in the European Pharmacopoeia (Ph. Eur.) and is required for each clinical batch of EPO as release-relevant test.

Efforts are being made at present to replace the biological reference preparation 1(BRP1) of EPO by the biological reference preparation 2 (BRP2). For this purpose, BRP1 of EPO was measured within the framework of a ring study with the "candidate biological reference preparation 2" (cBRP2) of EPO inter alia with the help of capillary zone electrophoresis and the analytical data thereby obtained were compared in detail (M-E. Behr-Gross, A. Daas, A. F. Bristow, Collaborative study for the establishment of erythropoietin BRP batch 2, Pharmeuropa Bio 2004-1, 23-33).

The underlying object of the present invention was therefore to provide a method which makes it possible to represent the complex data of capillary zone electrophoresis in a comparatively simplified and nevertheless meaningful, reliable and valid manner relative to the European Pharmacopoeia or Behr-Gross et al. (2004), the method requiring to be suitable for simplifying or replacing the known in vivo methods, e.g. for determination of the bioavailability and the batch consistency of sialoglycoproteins.

This object is achieved by the features of the method described herein and the advantageous developments thereof. Uses according to the invention are also described.

It was established surprisingly that the isoform number I determined via CZE of a sialoglycoprotein correlates outstandingly with the in vivo bioavailability and biological activity of a sialoglycoprotein. Because of the good reproducibility and the analytical precision of this determination, I can also be used advantageously in a method for establishing the batch consistency of a therapeutic glycoprotein.

The present tests lead to the conclusion that the "isoform status", which is made evident in CZE, and hence the "glycosylation status" of a sialoglycoprotein can be described in the simple number I very helpfully and meaningfully. Hence, by means of determination of I, the isoform distribution of a glycoprotein from batch to batch or within the framework of stability studies can be compared in a simple way.

There is understood by the "glycosylation status" of a glycoprotein in the context of the present invention, the composition of the glycans of the glycoprotein from bi-, tri-, and tetraantenary oligosaccharide structures and their respective sialylation degree, i.e. the content of bonded sialic acid, and also the content of sulphate- or phosphate groups, including the glycosylation value of the O-glycosidically cross-linked sialylated sugar chains.

There is understood by the bioavailability of a glycoprotein-therapeutic agent, the capacity of the therapeutic agent to develop its biological activity or therapeutic effectiveness in vivo. Accordingly, the bioavailability and the biological activity are determined crucially by the in vivo clearance behavior, i.e. the removal of the therapeutic agent from the blood circulation. For example, it is known for EPO that, in the absence of N-acetylneuraminic acid which is bonded in end position to the N-glycosidic sugar chains, it is removed very rapidly from the blood circulation via the so-called "asialo receptor" in the liver and hence cannot develop its biological effectiveness.

The isoform number I of a therapeutic glycoprotein correlates surprisingly with the in vivo half-life of the glycoprotein and hence represents a completely new measuring parameter which makes it possible to estimate in advance in a very simple manner the clearance behavior to be expected for the therapeutic glycoprotein from batch to batch. Consequently, I also enables a statement about the biological effectiveness to be expected for the glycoprotein from batch to batch. Hence when determining I of a therapeutic glycoprotein from batch to batch, for example the very complex, time-consuming, expensive and very imprecise determination of the therapeutic effectiveness of the glycoprotein in animal experiments (in vivo assay) can be dispensed with.

In addition, this makes possible a new and significant contribution to the reduction of animal experiments and hence to improved animal protection. At the same time, the isoform number I represents a particularly suitable measurement for the batch consistency of the glycoprotein.

Calculation of the isoform number I of a sialoglycoprotein is effected in that firstly the sialoglycoprotein is separated by means of capillary zone electrophoresis. Building upon the evaluation of the capillary zone electrophoresis, a product $i_n = m_n \cdot p_n$ is formed respectively from the percentage peak area component p of the isoform n ($p_n$), which is obtained via capillary zone electrophoresis, with a multiplier $m_n$, n being a whole number from 1 to 14, $m_n = x_n \cdot n$ and $x_n$ any number from the group of real numbers apart from 0. The thus obtained products $i_1$ to $i_n$ are summated subsequently to form the isoform number I $$I = \sum_{i=1}^{i=n} i_n$$

The sum of the percentage isoform components gives 100%.

For example, $x_n$ for each isoform =1, as a result of which the multiplier corresponds to the number of the corresponding isoform.

For example, $x_n$ can also be different however for each isoform and not equal to 1, as result of which the multiplier for each isoform is different. Preferably, $x_n$ is thereby a variable number which is calculated from the specific biological activity of the respective isoform. The specific activity of the isoforms for example of recombinant erythropoietin from CHO cells can be found for example in EP 0 428 267B1 (1997; Priority US 421444(1989).

The determination of I was verified on various batches of a therapeutic glycoprotein and applied to the comparison of EPO-BRP1 with EPO-cBRP2, known from the literature (M-E. Behr-Gross, A. Daas, A. F. Bristow, Collaborative study for the establishment of erythropoietin in BRP batch 2, Pharmeuropa Bio 2004-1, 23-33). It was thereby able to be shown that the isoform number I can be regarded as a new, meaningful, reliable and characteristic parameter for the isoform distribution or the protein glycosylation.

The method according to the invention is intended to be described in more detail with reference to the subsequent examples without wishing to restrict said method to the embodiments represented here.

The determination of I from the Collaborative Study of EPO (Behr-Gross et al., 2004) is found in the following as an example. For this purpose, the data published in Behr-Gross et al. (2004) were evaluated. The results obtained in the study are compiled in Table 1 or Table 3 for BRP1 and in Table 2 or Table 4 for cBRP2.

The study has revealed slight differences between BRP1 and cBRP2 which in the opinion of Behr-Gross et al. 2004 requires adaptation of the Ph. Eur. monograph.

The proportion of isoform 3 in cBRP2 is on average less than required by the Ph. Eur. monograph, whilst isoform 7 is very slightly below the upper limit of the current Ph. Eur. specification.

The present invention for in vitro evaluation of the quality and biological activity of EPO in particular or the quality of sialoglycoproteins in general has, relative to the state of the art (Hermentin et al. (1996) Glycobiology 6, 217-230; EP 0843821B1(2001), Priority DE 19527054 of 26.07.1995), the distinct advantage that the isoform determination can be implemented even with native glycoprotein and in a normal protein laboratory as long as the laboratory has capillary electrophoresis apparatus. In contrast, the state of the art requires for determination of the hypothetical charge number Z of a glycoprotein, with the help of which the biological activity of EPO can likewise be determined but in a much more difficult manner (Hermentin et al., ibid.), distinct expertise for release and isolation of the N-glycan pool (the N-glycosidically bonded sugar chains) of the glycoprotein which is then separated and analysed with respect to charge by means of anion exchange chromatography, in particular by means of "high-pH anion-exchange chromatography with pulsed amperometric detection" (HPAEC-PAD) (Hermentin et al., ibid.).

The isoform number I, the determination of which is effected already with the intact glycoprotein, makes it possible in particular to impart similarly meaningful information about the biological effectiveness, biological half-life, stability and batch consistency of EPO in general or of sialoglycoproteins which carry N-glycans as to how the hypothetical charge number Z (Hermentin et al., ibid.), the determination of which requires however significantly more complex and demanding technology and expertise.

As long as capillary electrophoresis of EPO is prescribed in a binding manner by the European Pharmacopoeia (Monograph 1316; Ph. Eur. Suppl. 5.3. (Erythropoietin concentrated solution), Strasbourg, France, Council of Europe; 2005) as release test for erythropoietin, so will the isoform number I presented here according to the invention be able to represent a simple, conclusive and reliable evaluation and release parameter for the quality of EPO preparations, i.e. the biological effectiveness thereof, biological half-life, batch consistency and storage stability.

The invention is explained in more detail by the subsequent examples 1 to 4.

EXAMPLE 1

Calculation of the isoform number I for EPO-BRP1 with reference to the data of the isoform distribution of EPO-BRP1 published by Behr-Gross et al. (2004); there thereby applies $x_n=1$ for each isoform for the product $i_n=m_n \cdot p_n$ with $m_n=x_n \cdot n$; n corresponds to the respective isoform number.

TABLE 1

| BRP1 | Lab 2 | | Lab 3 | | Lab 8 | | Lab 9 | | Lab 10 | | Lab 11 | |
|---|---|---|---|---|---|---|---|---|---|---|---|---|
| | Area % | $i_n$ | Area % | $i_n$ | Area % | $i_n$ | Area % | $i_n$ | Area % | $i_n$ | Area % | $i_n$ |
| I 0 | | | | | | | | | | | | |
| I 1 | 0.4 | 0.4 | 0.8 | 0.8 | 1.0 | 1.0 | 0.8 | 0.8 | 0.8 | 0.8 | 1.0 | 1.0 |
| I 2 | 1.9 | 3.8 | 2.5 | 5.0 | 3.1 | 6.2 | 2.2 | 4.4 | 2.4 | 4.8 | 2.7 | 5.4 |
| I 3 | 5.9 | 17.7 | 6.0 | 18.0 | 6.9 | 20.7 | 5.6 | 16.8 | 6.2 | 18.6 | 6.2 | 18.6 |
| I 4 | 18.4 | 73.6 | 18.3 | 73.2 | 17.8 | 71.2 | 19.1 | 76.4 | 17.7 | 70.8 | 19.0 | 76.0 |
| I 5 | 29.6 | 148.0 | 29.0 | 145.0 | 28.2 | 141.0 | 30.1 | 150.5 | 28.8 | 144.0 | 28.8 | 144.0 |
| I 6 | 28.7 | 172.2 | 27.9 | 167.4 | 27.5 | 165.0 | 24.4 | 146.4 | 28.5 | 171.0 | 27.8 | 166.8 |
| I 7 | 14.4 | 100.8 | 14.2 | 99.4 | 14.1 | 98.7 | 16.1 | 112.7 | 14.6 | 102.2 | 13.7 | 95.9 |
| I 8 | 0.7 | 5.6 | 1.3 | 10.4 | 1.4 | 11.2 | 1.8 | 14.4 | 0.9 | 7.2 | 0.8 | 6.4 |
| total | 100.0 | 522.1 | 100.0 | 519.2 | 100.0 | 515.0 | 100.1 | 522.4 | 99.9 | 519.4 | 100.0 | 514.1 |

As is evident from Table 1, for BRP1 from the data of six laboratories which took part in the Collaborative Study, the following isoform numbers were able to be determined:

| Lab 2: | I = 522.1 (rounded: I = 522) |
|---|---|
| Lab 3: | I = 519.2 (rounded: I = 519) |
| Lab 8: | I = 515.0 (rounded: I = 515) |
| Lab 9: | I = 522.4 (rounded: I = 522) |
| Lab 10: | I = 519.4 (rounded: I = 519) |
| Lab 11: | I = 514.1 (rounded: I = 514) |
| Average: | I = 518.7 (rounded: I = 519) |
| Standard deviation: | SD = 3.5 |
| Variation coefficient: | VC = 0.7% |

The data of Table 1 show that if $x_n=1$ for each isoform, from the CZE data for BRP1 of the six laboratories which took part in this Collaborative Study, an isoform number I between 514 and 522 can be calculated, which establishes the good comparability of the CZE analysis from laboratory to laboratory and also the high precision of the isoform number I.

EXAMPLE 2

Calculation of the isoform number I for EPO-cBRP2 by means of the data of the isoform distribution of EPO-cBRP2 published by Behr-Gross et al. (2004); there thereby applies $x_n=1$ for each isoform for the product $i_n=m_n \cdot pn$ with $m_n \cdot i = x_n \cdot n$; n corresponds to the respective isoform number.

deviation obvious (possibly a slight analysis error) for laboratory 11 for cBRP2 (in comparison with the other laboratories).

This circumstance is evident only via this evaluation of the isoform number I which is possible according to the present invention, which establishes the high degree of meaningfulness of this isoform number I with respect to the isoform distribution of EPO in particular or of sialoglycoproteins in general.

Furthermore, the difference, described in the Collaborative Study, between EPO-BRP1 and EPO-cBRP2 is evident via the isoform number in a simple and conclusive form. An

TABLE 2

| cBRP2 | Lab 2 | | Lab 3 | | Lab 8 | | Lab 9 | | Lab 10 | | Lab 11 | | Lab 12 | |
|---|---|---|---|---|---|---|---|---|---|---|---|---|---|---|
| | Area % | $i_n$ | Area % | $i_n$ | Area % | $i_n$ | Area % | $i_n$ | Area % | $i_n$ | Area % | $i_n$ | Area % | $i_n$ |
| I 0 | | | | | | | | | | | | | | |
| I 1 | | | | | 0.3 | 0.3 | 0.5 | 0.5 | 0.4 | 0.4 | 0.3 | 0.3 | 0.2 | 0.2 |
| I 2 | 1.0 | 2.0 | 1.0 | 2.0 | 1.6 | 3.2 | 0.9 | 1.8 | 1.3 | 2.6 | 1.5 | 3.0 | 1.0 | 2.0 |
| I 3 | 4.5 | 13.5 | 4.9 | 14.7 | 5.1 | 15.3 | 3.8 | 11.4 | 4.6 | 13.8 | 5.2 | 15.6 | 5.3 | 15.9 |
| I 4 | 16.8 | 67.2 | 16.8 | 67.2 | 16.2 | 64.8 | 17.3 | 69.2 | 15.4 | 61.6 | 19.0 | 76.0 | 17.3 | 69.2 |
| I 5 | 27.1 | 135.5 | 27.2 | 136.0 | 26.3 | 131.5 | 27.8 | 139.0 | 26.8 | 134.0 | 28.7 | 143.5 | 26.9 | 134.5 |
| I 6 | 30.4 | 182.4 | 29.7 | 178.2 | 30.0 | 180.0 | 29.4 | 176.4 | 30.4 | 182.4 | 30.0 | 180.0 | 29.6 | 177.6 |
| I 7 | 18.6 | 130.2 | 18.3 | 128.1 | 18.6 | 130.2 | 18.6 | 130.2 | 19.2 | 134.4 | 15.2 | 106.4 | 18.1 | 126.7 |
| I 8 | 1.7 | 13.6 | 2.1 | 16.8 | 1.8 | 14.4 | 1.8 | 14.4 | 1.9 | 15.2 | 0.1 | 0.8 | 1.7 | 13.6 |
| Total | 100.1 | 544.4 | 100.0 | 543.0 | 99.9 | 539.7 | 100.1 | 542.9 | 100.0 | 544.4 | 100.0 | 525.6 | 100.1 | 539.7 |

As is evident from Table 2, for cBRP2 from the data of the seven laboratories which took part in the Collaborative Study, the following isoform numbers were able to be determined:

| Lab 2: | I = 544.4 (rounded: I = 544) |
| Lab 3: | I = 543.0 (rounded: I = 543) |
| Lab 8: | I = 539.7 (rounded: I = 540) |
| Lab 9: | I = 542.9 (rounded: I = 543) |
| Lab 10: | I = 544.4 (rounded: I = 544) |
| Lab 11: | I = 525.6 (rounded: I = 526) |
| Lab 12: | I = 539.7 (rounded: I = 540) |
| Average: | AV = 540.0 (rounded: I = 540) |
| Standard deviation: | SD = 6.6 |
| Variation coefficient: | VC = 1.2% |

It is notable from the data of Table 2 that if $x_n=1$ for each isoform, from the CZE data for cBRP2 of the seven laboratories which took part in this Collaborative Study—with the exception of laboratory 11—, an isoform number I between 540 and 544 can be calculated, which establishes the good comparability of the CZE analysis from laboratory to laboratory and also the high precision of the isoform number I.

For laboratory 11, it is notable in this evaluation which is possible according to the present invention that the calculated isoform number with I=526 is significantly lower than in the remaining laboratories (I=540-544), which makes a slight average isoform number of I=519 was determined for EPO-BRP1 whilst an average isoform number of I=540 was calculated for EPO-cBRP2. This circumstance establishes the high degree of meaningfulness of the isoform number I with respect to the quality of EPO in general or of sialoglycoproteins in particular and the suitability of the isoform number I as a quality feature for the batch consistency, storage stability, biological half-life and the biological effectiveness of a therapeutic glycoprotein.

EXAMPLE 3

Calculation of the isoform number I for EPO-BRP1 with reference to the data of the isoform distribution of EPO-BRP1 published by Behr-Gross et al. (2004), taking into account the specific activity of the individual isoforms according to EP 0 428 267B1(1996; Priority US 421444 (1989)), based on the concentration determination at 280nm.

There thereby applies in the product $i_n=m_n \cdot p_n$ with $m_n=x_n \cdot n$ for $x_n$ respectively, the number mentioned in column U/mg (the specific isoform activity [U/mg] according to EP 0 428 267B1), divided by 100; n=1 is thereby valid for n respectively. The respective isoform number I hence reflects the biological activity of the EPO product in a particularly relevant manner.

TABLE 3

| BRP1 | U/mg | $x_n$ | Lab 2 | | Lab 3 | | Lab 8 | | Lab 9 | | Lab 10 | | Lab 11 | |
|---|---|---|---|---|---|---|---|---|---|---|---|---|---|---|
| | | | Area % | $i_n$ | Area % | $i_n$ | Area % | $i_n$ | Area % | $i_n$ | Area % | $i_n$ | Area % | $i_n$ |
| I 0 | | | | | | | | | | | | | | |
| I 1 | 50300 | 503 | 0.4 | 201 | 0.8 | 402 | 1.0 | 503 | 0.8 | 402 | 0.8 | 402 | 1.0 | 503 |
| I 2 | 70600 | 706 | 1.9 | 1341 | 2.5 | 1765 | 3.1 | 2189 | 2.2 | 1553 | 2.4 | 1694 | 2.7 | 1906 |
| I 3 | 96600 | 966 | 5.9 | 5699 | 6.0 | 5796 | 6.9 | 6665 | 5.6 | 5410 | 6.2 | 5989 | 6.2 | 5989 |
| I 4 | 170300 | 1703 | 18.4 | 31335 | 18.3 | 31165 | 17.8 | 30313 | 19.1 | 32527 | 17.7 | 30143 | 19.0 | 32357 |

TABLE 3-continued

| BRP1 | U/mg | $x_n$ | Lab 2 Area % | $i_n$ | Lab 3 Area % | $i_n$ | Lab 8 Area % | $i_n$ | Lab 9 Area % | $i_n$ | Lab 10 Area % | $i_n$ | Lab 11 Area % | $i_n$ |
|---|---|---|---|---|---|---|---|---|---|---|---|---|---|---|
| I 5 | 255800 | 2558 | 29.6 | 75717 | 29.0 | 74182 | 28.2 | 72136 | 30.1 | 76996 | 28.8 | 73670 | 28.8 | 73670 |
| I 6 | 258400 | 2584 | 28.7 | 74161 | 27.9 | 72094 | 27.5 | 71060 | 24.4 | 63050 | 28.5 | 73644 | 27.8 | 71835 |
| I 7 | 258700 | 2587 | 14.4 | 37253 | 14.2 | 36735 | 14.1 | 36477 | 16.1 | 41651 | 14.6 | 37770 | 13.7 | 35442 |
| I 8 | 205800 | 2058 | 0.7 | 1441 | 1.3 | 2675 | 1.4 | 2881 | 1.8 | 3704 | 0.9 | 1852 | 0.8 | 1646 |
| total | | | 100.0 | 227148 | 100.0 | 224815 | 100.0 | 222224 | 100.1 | 225293 | 99.9 | 225166 | 100.0 | 223349 |

As is evident from Table 3, for BRP1 from the data of the six laboratories which took part in the Collaborative Study, the following alternative isoform numbers which are likewise possible according to the present invention were able to be determined:

| Lab 2: | I = 227148 |
| Lab 3: | I = 224815 |
| Lab 8: | I = 222224 |
| Lab 9: | I = 225293 |
| Lab 10: | I = 225166 |
| Lab 11: | I = 223349 |
| Average: | I = 224666 |
| Standard deviation: | SD = 1704 |
| Variation coefficient: | VC = 0.8% |

The data of Table 3 show that from the CZE data for BRP1 of the six laboratories which took part in this Collaborative Study, an alternative (optionally possible) isoform number I between 222224 and 227148 can be calculated, which likewise establishes the good comparability of the CZE analysis from laboratory to laboratory and also the high precision of the alternatively possible isoform number I.

EXAMPLE 4

Calculation of the isoform number I for EPO-cBRP2 with reference to the data of the isoform distribution of EPO-cBRP2 published by Behr-Gross et al. (2004), taking into account the specific activity of the individual isoforms according to EP 0 428 267B1(1996; Priority US 421444 (1989), based on the concentration determination at 280nm.

There thereby applies in the product $i_n = m_n \cdot p_n$ with $m_n = x_n \cdot n$ for $x_n$ respectively, the number mentioned in column U/mg (the specific isoform activity [U/mg] according to EP 0 428 267B1), divided by 100; there thereby applies for n respectively n=1. The respective isoform number I hence reflects the biological activity of the EPO product in a particularly relevant manner.

TABLE 4

| cBRP2 | U/mg | $x_n$ | Lab 2 Area % | $i_n$ | Lab 3 Area % | $i_n$ | Lab 8 Area % | $i_n$ | Lab 9 Area % | $i_n$ | Lab 10 Area % | $i_n$ | Lab 11 Area % | $i_n$ | Lab 12 Area % | $i_n$ |
|---|---|---|---|---|---|---|---|---|---|---|---|---|---|---|---|---|
| I 0 | | | | | | | | | | | | | | | | |
| I 1 | 50300 | 503 | | 0 | | 0 | 0.3 | 151 | 0.5 | 252 | 0.4 | 201 | 0.3 | 151 | 0.2 | 101 |
| I 2 | 70600 | 706 | 1.0 | 706 | 1.0 | 706 | 1.6 | 1130 | 0.9 | 635 | 1.3 | 918 | 1.5 | 1059 | 1.0 | 706 |
| I 3 | 96600 | 966 | 4.5 | 4347 | 4.9 | 4733 | 5.1 | 4927 | 3.8 | 3671 | 4.6 | 4444 | 5.2 | 5023 | 5.3 | 5120 |
| I 4 | 170300 | 1703 | 16.8 | 28610 | 16.8 | 28610 | 16.2 | 27589 | 17.3 | 29462 | 15.4 | 26226 | 19.0 | 32357 | 17.3 | 29462 |
| I 5 | 255800 | 2558 | 27.1 | 69322 | 27.2 | 69578 | 26.3 | 67275 | 27.8 | 71112 | 26.8 | 68554 | 28.7 | 73415 | 26.9 | 68810 |
| I 6 | 258400 | 2584 | 30.4 | 78554 | 29.7 | 76745 | 30.0 | 77520 | 29.4 | 75970 | 30.4 | 78554 | 30.0 | 77520 | 29.6 | 76486 |
| I 7 | 258700 | 2587 | 18.6 | 48118 | 18.3 | 47342 | 18.6 | 48118 | 18.6 | 48118 | 19.2 | 49670 | 15.2 | 39322 | 18.1 | 46825 |
| I 8 | 205800 | 2058 | 1.7 | 3499 | 2.1 | 4322 | 1.8 | 3704 | 1.8 | 3704 | 1.9 | 3910 | 0.1 | 206 | 1.7 | 3499 |
| total | | | 100.1 | 233156 | 100.0 | 232036 | 99.9 | 230414 | 100.1 | 232924 | 100.0 | 232477 | 100.0 | 229053 | 100.1 | 231008 |

As is evident from Table 4, for cBRP2 from the data of the seven laboratories which took part in the Collaborative Study, the following alternative isoform numbers which are likewise possible according to the present invention were able to be determined:

| Lab 2: | I = 233156 |
| Lab 3: | I = 232036 |
| Lab 8: | I = 230414 |
| Lab 9: | I = 232924 |
| Lab 10: | I = 232477 |
| Lab 11: | I = 229053 |
| Lab 12: | I = 231008 |
| Average: | MW = 231581 |
| Standard deviation: | SD = 1493 |
| Variation coefficient: | VC = 0.6% |

It is notable from the data of Table 4 that from the CZE data for cBRP2 of the seven laboratories which took part in this Collaborative Study, an alternative (optionally possible) isoform number I between 229053 and 233156 can be calculated, which likewise establishes the good comparability of the CZE analysis from laboratory to laboratory and also the high precision of the isoform number I.

According to this (optionally possible) evaluation, the results from laboratory 11 in comparison with the remaining results are not significant.

Furthermore, the difference between EPO-BRP1 and EPO-cBRP2, described in the Collaborative Study, is also evident via this optionally possible calculation of the isoform number according to the present invention in a simple and conclusive manner. For EPO-BRP1, an average isoform number of I=224666 was determined, whilst an average isoform number of I=231581 was calculated for EPO-cBRP2. Also this optionally possible calculation of the isoform number according to the present invention establishes the high degree of meaningfulness of the isoform number with respect to the quality of EPO in general or of sialoglycoproteins in particular and the suitability of the isoform number I as a quality feature for the batch consistency, storage stability, biological half-life and the biological effectiveness of a therapeutic glycoprotein.

The invention claimed is:

1. Method for characterising the quality of sialoglycoproteins by an isoform number I, in which
   a) the sialoglycoprotein is separated by means of capillary zone electrophoresis,
   b) the product $i_n = m_n \cdot p_n$ is formed from the percentage peak area component p of the isoform n ($p_n$), which is obtained via capillary zone electrophoresis, with a multiplier $m_n$, n being a whole number from 1 to 14, $m_n = x_n \cdot n$ and $x_n$ any number from the group of real numbers apart from 0, and
   c) the thus obtained products $i_1$ to $i_n$ are summated to form the isoform number I.

2. Method according to claim 1, wherein the sialoglycoprotein is a human sialoglycoprotein.

3. Method according to claim 1, wherein the sialoglycoprotein is a recombinant human sialoglycoprotein.

4. Method according to claim 1, wherein the sialoglycoprotein is erythropoietin.

5. Method according to claim 1, wherein the sialoglycoprotein is follicle-stimulating hormone.

6. Method according to claim 1, wherein the sialoglycoprotein is chorionic gonadotrophin.

7. Method according to claim 1, wherein n is a whole number from 1 to 8.

8. Method according to claim 1, wherein $x_n = 1$.

9. Method according to claim 1, wherein $x_n$ is calculated from the specific activity of the respective isoform n or in that the specific activity of the respective isoform n goes into $x_n$.

10. Method according to claim 1, wherein the isoform number I represents a quality feature for the biological effectiveness of the sialoglycoprotein.

11. Method according to claim 10, wherein the biological effectiveness of the sialoglycoprotein is assessed by comparison with the specific isoform number of a sialoglycoprotein standard.

12. Method according to claim 1, wherein the isoform number I represents a quality feature for the batch-to-batch consistency of the sialoglycoprotein.

13. Method according to claim 12, wherein the batch consistency of the sialoglycoprotein is assessed by comparison with the specific isoform number of a sialoglycoprotein standard.

14. Method according to claim 1, wherein the isoform number I represents a quality feature for the storage stability of the sialoglycoprotein.

15. Method according to claim 14, wherein the storage stability of the sialoglycoprotein is assessed by comparison with the specific isoform number of a sialoglycoprotein standard.

16. Method according to claim 1, wherein the isoform number I represents a quality feature for the biological half-life of the sialoglycoprotein.

17. Method according to claim 16, wherein the biological half-life of the sialoglycoprotein is assessed by comparison with the specific isoform number of a sialoglycoprotein standard.

18. Method according to claim 9, wherein $x_n = 1$.

* * * * *